United States Patent [19]

Wagner et al.

[11] 3,943,180

[45] Mar. 9, 1976

[54] 2,4-BIS-(TRIFLUOROMETHYL)-6-NITROPHENOL COMPOUNDS AND HERBICIDAL COMPOSITIONS

[75] Inventors: Klaus Wagner; Ludwig Eue; Robert R. Schmidt; Ernst Roos, all of Cologne, Germany

[73] Assignee: Bayer Aktiengesellschaft, Leverkusen, Germany

[22] Filed: July 17, 1974

[21] Appl. No.: 489,206

Related U.S. Application Data

[62] Division of Ser. No. 335,400, Feb. 23, 1973, Pat. No. 3,894,079.

[30] Foreign Application Priority Data

Feb. 29, 1972  Germany............................ 2209528

[52] U.S. Cl. ...... 260/622 R; 260/621 P; 260/623 D; 260/468 E; 260/479 R; 260/567.1; 71/122; 260/579 C; 260/579 S
[51] Int. Cl.².................... C07C 79/26; C07C 39/26
[58] Field of Search ........ 260/622 R, 623 D, 621 P; 71/122

[56] References Cited
UNITED STATES PATENTS 3,251,889   5/1966   Kulka.................................. 260/622

*Primary Examiner*—James O. Thomas, Jr.
*Assistant Examiner*—W. B. Lone
*Attorney, Agent, or Firm*—Burgess, Dinklage & Sprung

[57] ABSTRACT

Novel 2,4-bis-(trifluoromethyl)-6-nitrophenol compounds of the formula

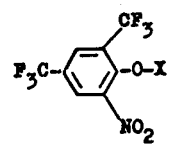

in which

X is hydrogen; M; HN⁺R¹R²R³; —COR⁴; —COOR⁵; N,N-dimethylaminocarbonyl;  —SO₂R⁶  or —CO—NH—R⁷;

M is an equivalent of an alkali metal or alkaline earth metal,

R¹, R² and R³ (individually) are hydrogen, alkyl, alkoxyalkyl, alkenyl, hydroxyalkyl, cycloalkyl, phenylalkyl, phenyl or substituted phenyl, R⁴ and R⁵ individually are alkyl, substituted alkyl, alkenyl, phenyl or substituted phenyl, R⁶ is alkyl, substituted alkyl, phenyl, substituted phenyl or dimethylamino, and R⁷ is alkyl, alkenyl, cycloalkyl, phenyl or substituted phenyl; are outstandingly effective selective herbicides.

3 Claims, No Drawings

2,4-BIS-(TRIFLUOROMETHYL)-6-NITROPHENOL COMPOUNDS AND HERBICIDAL COMPOSITIONS

This is a division, of application Ser. No. 335,400, filed Feb. 23, 1973 now U.S. Pat. No. 3,894,079.

The present invention relates to certain new 2,4-bis-(trifluoromethyl)-6-nitrophenol compounds, to herbicidal compositions containing them and to their use as herbicides.

It is known that 2,4-dinitro-6-alkylphenol derivatives, for example 2,4-dinitro-6-sec.-butylphenol acetate (Dinoseb acetate) (cf. Deutsche Auslegeschriften (German Published Specifications) 1 088 757 and 1 103 072), can be used as herbicides.

The present invention provides 2,4-bis-(trifluoromethyl)-6-nitrophenol derivatives of the general formula

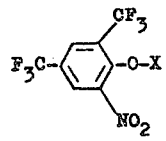

(I)

in which

X is hydrogen; M; HN$^+$R$^1$R$^2$R$^3$ (i.e., quaternary ammonium); —COR$^4$ (i.e., hydrocarbylcarbonyl); —COOR$^5$ (i.e., hydrocarbyloxycarbonyl), N,N-dimethylaminocarbonyl; —SO$_2$R$^6$ (i.e., substituted sulfonyl); or —CO—NH—R$^7$ (i.e., hydrocarbylamido), M is an equivalent of an alkali metal or alkaline earth metal, R$^1$, R$^2$ and R$^3$ (which may be the same or different) are hydrogen, alkyl, alkoxyalkyl, alkenyl, hydroxyalkyl, cycloalkyl, phenylalkyl, phenyl or substituted phenyl, R$^4$ and R$^5$ individually are alkyl, substituted alkyl, alkenyl, phenyl or substituted phenyl, R$^6$ is alkyl, substituted alkyl, phenyl, substituted phenyl or dimethylamino, and R$^7$ is alkyl, alkenyl, cycloalkyl, phenyl or substituted phenyl.

Surprisingly, the new 2,4-bis-(trifluoromethyl)-6-nitrophenol derivatives show stronger herbicidal properties than the previously known 2,4-dinitro-6-alkylphenol derivatives and moreover are also of good effectiveness selectively. The active compounds according to the invention therefore represent a valuable enrichment of the art.

Preferred, because of their high activity, are compounds wherein M is lithium, potassium or sodium or an equivalent of a calcium or barium ion; R$^1$, R$^2$ and R$^3$ are hydrogen, alkyl of from 1 to 12 carbon atoms, alkoxyalkyl of from 1 to 4 carbon atoms in each of the alkoxy and alkyl moieties, alkenyl of from 2 to 4 carbon atoms, cycloalkyl of from 5 or 6 carbon atoms in the ring system, phenylalkyl of from 1 or 2 carbon atoms in the alkyl moiety, or for phenyl (which may be substituted by chlorine, bromine, trifluoromethyl, nitro and/or methyl); R$^4$ and R$^5$ are alkyl of from 1 to 12 carbon atoms, or for (possibly substituted by chlorine, bromine or trifluoromethyl) alkyl of from 1 to 12 carbon atoms or alkenyl of from 2 to 4 carbon atoms, or for phenyl (which may be substituted by chlorine, bromine, trifluoromethyl, nitro and/or methyl); R$^6$ is C$_{1-4}$ alkyl which may be substituted by chlorine, bromine or trifluoromethyl, or R$^6$ is phenyl (which may be substituted by chlorine, bromine, trifluoromethyl, nitro and/or methyl) or dimethylamino; and R$^7$ is alkyl of from 1 to 4 carbon atoms, alkenyl of from 2 to 4 carbon atoms, cycloalkyl of from 5 to 6 carbon atoms in the ring system or for phenyl (which may be substituted by chlorine, bromine, trifluoromethyl, nitro and/or methyl).

The invention also provides a process for the production of a 2,4-bis-(trifluoromethyl)-6-nitrophenol derivative of formula (I) (in which X is not hydrogen) in which process 2,4-bis-(trifluoromethyl)-6-nitrophenol of the formula

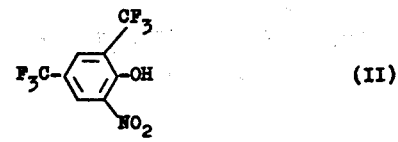

(II)

is reacted with the appropriate member of the following group of compounds:

a. a compound of the formula

(III)

b. an amine of the formula

(IV)

c. an acid chloride of the formula

(V)

d. a chloroformic acid ester of the formula

(VI)

e. dimethylcarbamic acid chloride of the formula

(VII)

f. a sulphonyl chloride of the formula

(VIII)

g. an isocyanate of the formula

(IX), the symbols M and R$^1$ to R$^7$ in the formulae (III–IX) possessing the meanings stated above.

The reaction may be effected optionally in the presence of a diluent and optionally in the presence of an acid-binding agent. The reaction is of a type which is known per se, and it may be effected in any convenient way.

If, according to process variant (a), sodium hydroxide is used as starting material, the reaction course is represented by the following scheme:

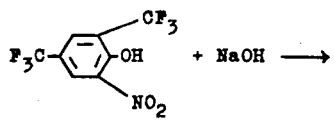 + NaOH ⟶

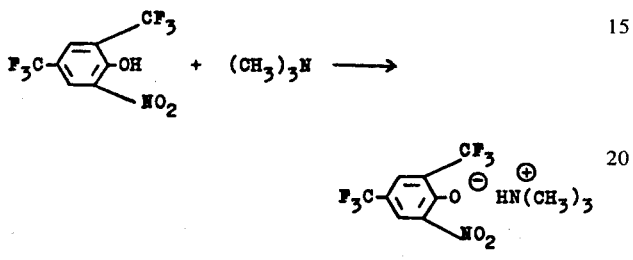 + $H_2O$

If in process variant (b), trimethylamine is used, the reaction proceeds according to the following scheme:

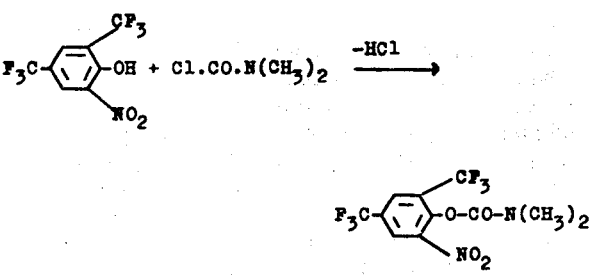 + $(CH_3)_3N$ ⟶

If, according to process variant (c), crotonic acid chloride is used, the reaction course can be represented by the following scheme:

$F_3C$—⟨⟩—OH + $Cl.CO.CH=CH.CH_3$ $\xrightarrow{-HCl}$

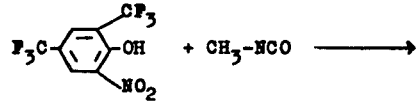

If, according to process variant (d), chloroformic acid ethyl ester is used, the reaction course can be represented by the following scheme:

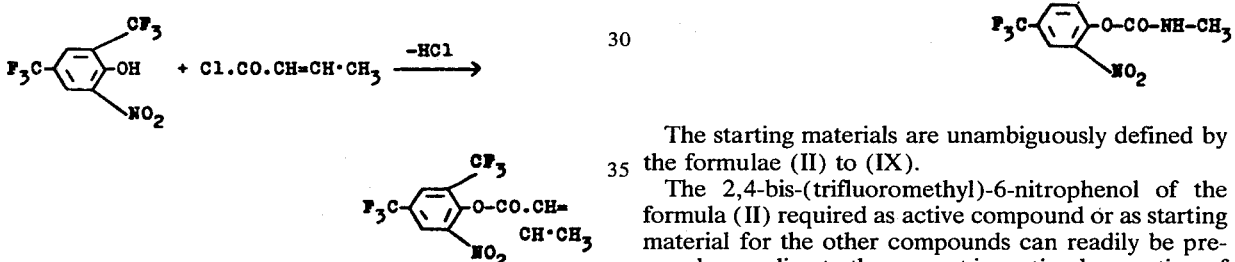

If according to process variant (e), N,N-dimethylcarbamic acid chloride is used as starting material, the following formula scheme applies:

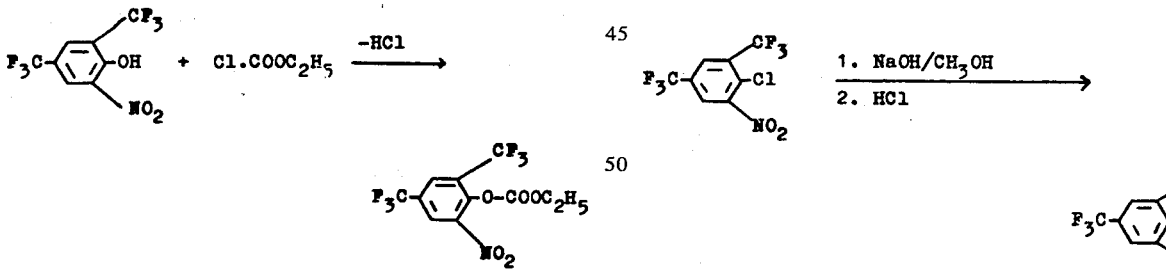

If, according to process variant (f), methane-sulphochloride is used, the reaction course can be represented by the following scheme:

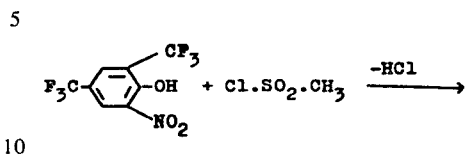

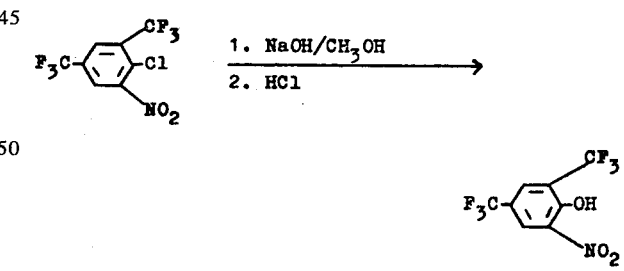

If, according to process variant (g), methylisocyanate is used, the reaction proceeds as follows:

$F_3C$—⟨⟩—OH + $CH_3$-NCO ⟶

$F_3C$—⟨⟩—O-CO-NH-$CH_3$

The starting materials are unambiguously defined by the formulae (II) to (IX).

The 2,4-bis-(trifluoromethyl)-6-nitrophenol of the formula (II) required as active compound or as starting material for the other compounds can readily be prepared according to the present invention by reaction of 2,4-bis-(trifluoromethyl)-6-nitrochlorobenzene (known from the literature) with an alkali, for example 2 moles of sodium hydroxide in boiling methanol (cf. Example 1):

$F_3C$—⟨⟩—Cl $\xrightarrow[2.\ HCl]{1.\ NaOH/CH_3OH}$ $F_3C$—⟨⟩—OH

The compounds of the formula (III) are known. Examples include: lithium, sodium, potassium and calcium hydroxide.

The compounds of the formula (IV) are known. Examples include: ammonia, dimethylamine, diethylamine, triethylamine, dicyclohexylamine, butylamine and 2-hydroxypolylamine.

The acid chlorides of the formula (V) are described in the literature. Examples include: acetyl, trifluoroacetyl, propionyl, α-chloropropionyl, n-butyryl chloride, acrylic acid chloride, methacrylic acid chloride, dimethyl-acrylic acid chloride, crotonyl, benzoyl, p-chlorobenzoyl, o-nitrobenzoyl and m-toluyl chlorides.

The chloroformic acid esters of the formula (VI) are likewise known. Examples include: chloroformic acid methyl, ethyl, propyl, isopropyl, n-butyl, n-hexyl and phenyl esters.

The sulphochlorides of the formula (VIII) are likewise known from the literature. Examples include: methane-, chloromethane-, β-chloroethane-sulfonyl chloride, benzene-, 3,4-dichloro-benzene- and 4-chlorobenzenes-sulfochlorides.

The isocyanates of the formula (IX) are also known from the literature. Examples include: methyl, ethyl, propyl, butyl, allyl, cyclohexyl, phenyl, 3-chlorophenyl and 4-nitrophenyl isocyanates.

Preferred diluents, for the process variants (*a*) and (*b*) are water/$C_{1-6}$ alcohol mixtures; and, specifically for process variant (*b*), inert organic solvents, such as benzene, acetone, acetonitrile.

For the process variants (*c*) – (*g*), preferred diluents are inert organic solvents. These include hydrocarbons, such as benzene, chlorobenzene, toluene and xylene; ethers, such as diethyl ether, dibutyl ether, tetrahydrofuran and dioxan; esters, such as ethyl acetate; ketones, such as acetone and methyl ethyl ketone; and nitriles, such as acetonitrile and propionitrile.

Process variants (*a*) and (*b*) are susually so carried out that a solution of the 2,4-bis-(trifluoromethyl)-6-nitrophenol in one of the solvents mentioned is reacted portionwise with at least the equimolar amount of a compound of the formula (III) or (IV).

Process variant (*c*) to (*f*) are preferably so carried out that a solution of 2,4-bis-(trifluromethyl)-6-nitrophenol in one of the solvents mentioned is provided in the presence of an acid-binding agent, preferably a tertiary amine such as triethylamine, N,N-dimethylbenzylamine, diethylaniline, pyridine, picoline or quinoline or an alkaline-reacting inorganic substance such as potassium carbonate or sodium carbonate, and the reactive chlorine compound concerned of the formulae (V) to (VIII) is added portionwise, with stirring.

Process variant (*g*) is usually so carried out that a solution of the 2,4-bis-(trifluoromethyl)-6-nitrophenol in one of the solvents mentioned above is reacted portionwise, in the presence of a catalyst, preferably triethylamine, with an isocyanate of the formula (IX). The starting materials are preferably used in stoichiometric amounts.

The reaction temperatures in all process variants can be varied within a fairly wide range. In general, the reaction is carried out in a range from −10° to +120°C, preferably +10° to +80°C.

The working up of the reaction mixtures may be carried out in customary manner. The purification of the reaction products can, if necessary, be effected by recrystallization from organic solvents, in particular from alcohols such as methanol or ethanol.

The preparation of the compounds of the invention is illustrated by the following Examples.

EXAMPLE 1

Preparation of 2,4-bis(trifluoromethyl)6-nitro-phenol

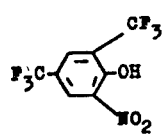  (Compound 1)

To a solution of 168 g (4 moles +5% excess) of sodium hydroxide in 1000 ml methanol there were added portionwise, at 50°–65°C internal temperature, 586 g (2 moles) 2,4-bis-trifluoromethyl-6-nitrochlorobenzene; the reaction mixture, after completion of addition (about 1 hour) of the reactive chlorine compound, was boiled under reflux for one hour. After cooling, 700 ml of water were added to the mixture and unreacted starting materials were extracted once with 400 ml methylene chloride. The aquous phase was separated off, distinct acidification was effected with 20%-strength sulfuric acid; the 2,4-bis-trifluoromethyl-6-nitrophenol which separated was taken up in methylene chloride. The organic phase was dried over sodium sulfate. The 2,4-bis-trifluoromethyl-6-nitro-phenol remaining behind after methylene chloride had been distilled off was subjected to vacuum distillation. 480 g (87%) of the boiling pont 105°–106°C/20 mm Hg were obtained; refractive index $n_D^{20}$ : 1.4580.

EXAMPLE 2

Preparation of 2,4bis-(trifluoromethyl)-6-nitrophenyl-sulfonic acid phenyl ester

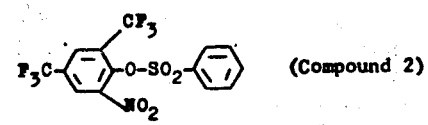  (Compound 2)

To a solution of 55 g (0.2 mole) 2,4-bis-(trifluoromethyl)-6-nitrophenol in 160 ml acetonitrile were added 16 g (0.1 mole +5% excess) of dry potassium carbonate, and heating to 70°–80°C was effected for 10 minutes. The reaction mixture was cooled to 10°C and 35.2 g (0.2 mole) benzenesulphonyl chloride were added and the mixture was kept at 60°–70 °C for 6 hours. After cooling, pouring into ice water was effected and the precipitated 2,4-bis-(trifluoromethyl)-6-nitrophenyl-sulfonic acid phenyl ester was filtered off with suction. 67 g (80%) of the product were obtained in the form of colorless crystals of the melting point 83°–84°C.

EXAMPLE 3

Preparation of 2,4-bis-(trifluoromethyl)-6-nitrophenyl-N-methylcarbamate

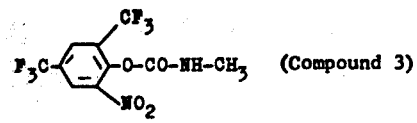  (Compound 3)

To a solution of 1100 g (4 moles) 2,4-bis-(trifluoromethyl)-6-nitrophenol and 5 ml triethylamine in 2500 ml light petroleum there were added dropwise in 1.5 hours, with stirring, 250 g (4 moles +10% excess) methyl isocyanate, and the reaction mixture was kept at 40°C for a further 10 hours. After cooling, the thick crystal slurry was filtered off with suction, again washed out with petroleum ether and subsequently with water. 1200 g (91%) of 2,4-bis-(trifluoromethyl)-6-nitro-phenyl-N-methylcarbamate were obtained in the form of colorless, melted, small needles of the melting point 124°–126°C.

EXAMPLE 4

Preparation of 2,4-bis-(trifluoromethyl)-6-nitro-phenol triethylammonium salt

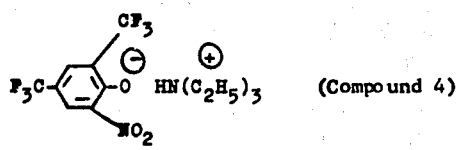 (Compound 4)

To a solution of 275 g (1 mole) 2,4-bis-(trifluoromethyl)-6-nitrophenol in 500 ml benzene there were added portionwise (exothermic) 110 g (1 mole +10% excess) triethylamine. The mixture was afterwards stirred for 3 hours at 20°C and excess solvent was removed in a vacuum. 376 g (100%) of triethylammonium salt of 2,4-bis-(trifluoromethyl)-6-nitrophenol were obtained in the form of an orange oil of the refractive index $n_D^{20}$ : 1.4895.

In analogous manner, the 2,4-bis-(trifluoromethyl)-6-nitrophenol derivatives of the following Examples 5–28 were prepared.

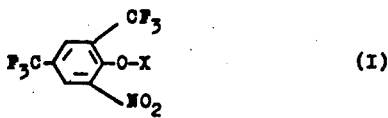 (I)

Table

| Example | X | Melting point (°C) |
|---|---|---|
| 5 | COOCH₃ | 63–65 |
| 6 | COOC₂H₅ | 52–53 |
| 7 | COO-i-C₃H₇ | 47–48 |
| 8 | COO—C₄H₉-n | 34–35 |
| 9 | COO—CH₂CH₂Cl | 64–66 |
| 10 | COCH₃ | 72–73 |
| 11 | COC₂H₅ | 38–40 |
| 12 | CO—C₆H₅ | 73–75 |
| 13 | CO—CH=CH—CH₃ | 62–64 |
| 14 | CO—CH=CH₂ | 42–43 |
| 15 | SO₂—CH₃ | 62–64 |
| 16 | CO—NH—C₃H₇-n | 93 |
| 17 | CO—NH—C₆H₅ | 105–107 |
| 18 | CO—NH—C₆H₄—Cl(m) | 98–99 |
| 19 | CO—NH—C₆H₄—Cl(p) | 112–113 |
| 20 | CO—NH—C₂H₅ | 104–106 |
| 21 | CO—NH—C₄H₉-n | 79–80 |
| 22 | CO—NH—⟨H⟩ | 98–99 |
| 23 | CO—C₆H₄—Cl(o) | 93–95 |
| 24 | H₂N⁺—⟨H⟩)₂ | 186–187 |
| 25 | H₃N⁺—CH₂—CH—CH₃ <br>                 OH | 139–140 |

Table-continued

| Example | X | Melting point (°C) |
|---|---|---|
| 26 | H₃N⁺—C₄H₉ | 176–177 |
| 27 | H₂N⁺—(C₂H₅)₂ | 109–110 |
| 28 | HN⁺(CH₃)₃ | 127–129 |

The IR and NMR spectra agreed completely with the structures given for Examples 1–28.

The active compounds according to the invention exhibit strong herbicidal properties and can therefore be used for the control of weeds. By weeds in the widest sense are meant all plants which grow in places where they are not desired. Whether the substances according to the invention act as total or selective herbicides depends largely on the amount applied.

The substances according to the invention can be used for example in the case of the following plants: dicotyledons, such as mustard (*Sinapis*), cress (*Lepidium*), cleavers (*Galium*), chickweed (*Stellarig*), chamomile (*Matricaria*), gallant soldier (*Galinsoga*), goosefoot (*Chenopodium*), annual nettle (*Urtica*), groundsel (*Senecio*) cotton (*Gossypium*), beets (*Beta*), carrots (*Daucus*), beans (*Phaseolus*), potatoes (*Solanum*), coffee (*Coffea*); monocotyledons, such as timothy (*Phleum*), bluegrass (*Poa*), fescue (*Festuca*), Eleusine (*Eleusine*), foxtail (*Setaria*), ryegrass (*Lolium*), cheat (*Bromus*), barnyard grass (*Echinochloa*), maize (*Zea*), rice (*Oryza*), oats (*Avena*), barley (*Hordeum*), wheat (*Triticum*), millet (*Panicum*), sugar cane (*Saccharum*).

The active compounds are particularly well suited for the selective control of weeds in cotton and cereals, including maize.

The active compound according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents, and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl napthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl. ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, e.g. aerosal propellants, such as halogenated hydrocarbons, e.g. freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents inlcude lignin, sulfite waste liquors and methyl cellulose.

The active compounds according to the invention may be present in the formulations in admixture with other active compounds.

The formulations contain, in general, from 0.1 to 95 per cent by weight of active compound, preferably 0.5 to 90 per cent by weight.

The active compounds may be applied as such or in the form of their formulations or the application forms prepared therefrom, such as ready-to-use solutions, emulsions, suspensions, powders, pastes and granulates. Application may take place in the usual manner, for example by watering, spraying, atomizing, dusting or scattering.

The active compounds according to the invention may be applied both according to the pre-emergence method and according to the post-emergence method, that is to say before or after emergence of the plants.

When the active compounds are used either according to the post-emergence method or the pre-emergence method, the amount applied can be varied within fairly wide ranges. In general, it is from 0.5 to 15 kg of active compound per hectare, preferably 1 to 6 kg per hectare.

The active compounds according to the invention also exhibit a fungicidal, bactericidal and soil-insecticidal activity; they further possess an effectiveness against plant-damaging insects and mites as well as against hygiene pests and pests of stored products.

The invention therefore provides a herbicidal composition containing as active ingredient a compound according to the invention in admixture with a solid or liquefied gaseous diluent or carrier or in admixture with a liquid diluent or carrier containing a surface-active agent.

The invention also provides a method of combating weeds which comprises applying to the weeds or their habitat a compound according to the invention alone or in the form of a composition containing as active ingredient a compound according to the invention in admixture with a diluent or carrier.

The invention also provides means of providing crops protected from damage by weeds by being grown in areas in which, immediately prior to and/or during the time of the growing, a compound according to the invention was applied alone or in admixture with a diluent or carrier. It will be seen that the usual methods of providing a harvested crop may be improved by the present invention.

The compounds according to the invention, and the preparation and use of the compounds according to the invention, are illustrated by the following Examples. In Table A and B the numbers of the compounds (in brackets) are those of the corresponding preparative Examples.

EXAMPLE A

Pre-emergence test
Solvent: 5 parts by weight acetone
Emulsifier: 1 part by weight alkylarylpolyglycol ether To produce a suitable preparation of active compound, 1 part by weight of active compound was mixed with the stated amount of solvent, the stated amount of emulsifier was added and the concentrate was then diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the test plants was determined and characterized by the values 0-5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or nor emerged.

The active compounds, the amounts applied and the results obtained can be seen from the following Table A.

Table A

| Active compound | Pre-emergence test | | | | | | | | |
|---|---|---|---|---|---|---|---|---|---|
| | Active compound applied kg/hectare | Chenopodium | Sinapis | Stellaria | Galinsoga | Matricaria | Cotton | Wheat | Maize |
|  (known: Dinoseb acetate) | 5<br>2.5 | 3<br>1 | 5<br>4 | 2<br>1 | 4<br>3 | 5<br>5 | 2<br>1 | 2<br>1 | 2<br>2 |
|  (1) | 5<br>2.5 | 5<br>5 | 5<br>5 | 4–5<br>4 | 5<br>5 | 5<br>4 | 3<br>3 | 5<br>3 | 1<br>0 |

Table A-continued

| Active compound | Active compound applied kg/hectare | Pre-emergence test Chenopodium | Sinapis | Stellaria | Galinsoga | Matricaria | Cotton | Wheat | Maize |
|---|---|---|---|---|---|---|---|---|---|
| 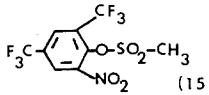 (15) | 5<br>2.5 | 5<br>5 | 5<br>5 | 4–5<br>3 | 5<br>5 | 5<br>4 | 1<br>0 | 4<br>3 | 1<br>1 |
| 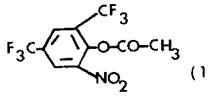 (10) | 5<br>2.5 | 5<br>5 | 5<br>5 | 4<br>3 | 5<br>5 | 5<br>5 | 1<br>0 | 4<br>3 | 0<br>0 |
| 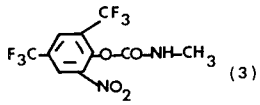 (3) | 5<br>2.5 | 5<br>5 | 5<br>5 | 4–5<br>4 | 5<br>5 | 5<br>5 | 4<br>3 | 3<br>1 | 1<br>0 |
| 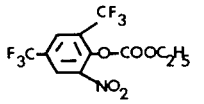 (6) | 5<br>2.5 | 5<br>5 | 5<br>5 | 4–5<br>4 | 5<br>4 | 4<br>3 | 2<br>1 | 3<br>2 | 2<br>1 |
| 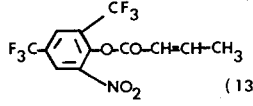 (13) | 5<br>2.5 | 5<br>5 | 5<br>5 | 4<br>3 | 5<br>5 | 5<br>5 | 3<br>2 | 4<br>3 | 1<br>1 |
| 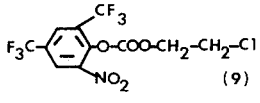 (9) | 5<br>2.5 | 5<br>5 | 5<br>5 | 4–5<br>4 | 5<br>5 | 5<br>5 | 1<br>0 | 2<br>1 | 1<br>0 |
| 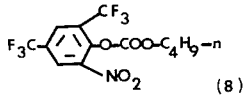 (8) | 5<br>2.5 | 5<br>5 | 5<br>5 | 4<br>3 | 5<br>5 | 5<br>5 | 3<br>1 | 2<br>1 | 1<br>0 |
| 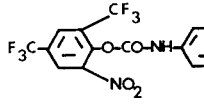 (17) | 5<br>2.5 | 5<br>5 | 5<br>5 | 4<br>3 | 5<br>5 | 5<br>5 | 2<br>1 | 2<br>1 | 1<br>0 |
| 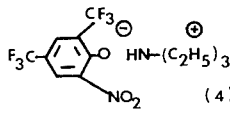 (4) | 5<br>2.5 | 5<br>5 | 5<br>5 | 4<br>3 | 5<br>5 | 4–5<br>4 | 3<br>1 | 3<br>2 | 1<br>0 |

EXAMPLE B

Post-emergence test

Solvent: parts by weight acetone
Emulsifier: 1 part by weight alkylarylpolyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound so that the amounts of active compound per unit area which are stated in the Table were applied. Depending on the concentration of the spray liquor, the amount of water applied lay between 1000 and 2000 liters/hectare. After three weeks, the degree of damage to the plants was determined and characterized by the values 0–5, which have the following meaning:

0 no effect
1 a few slightly burnt spots
2 marked damage to leaves
3 some leaves and parts of stalks partially dead
4 plant partially destroyed
5 plant completely dead.

The active compounds, the amounts applied and the results can be seen from the following Table B.

Table B

| Active compound | Active compound applied kg/hectare | Post-emergence test Echinochloa | Chenopodium | Sinapis | Urtica | Matricaria | Daucus | Cotton | Wheat |
|---|---|---|---|---|---|---|---|---|---|
| Dinoseb acetate (known) | 2<br>1 | 1<br>1 | 5<br>5 | 5<br>5 | 5<br>3 | 0<br>0 | 4<br>3 | 2<br>2 | 2<br>2 |
| (1) | 2<br>1 | 5<br>4 | 5<br>4 | 5<br>5 | 5<br>5 | 4<br>3 | 5<br>5 | 2<br>0 | 2<br>1 |
| (12) | 2<br>1 | 4–5<br>4 | 5<br>5 | 5<br>4 | 4<br>3 | 5<br>4 | 4<br>3 | 0<br>0 | 3<br>1 |
| (3) | 2<br>1 | 5<br>3–4 | 5<br>5 | 5<br>5 | 5<br>4–5 | 5<br>4–5 | 5<br>5 | 1<br>0 | 2<br>1 |
| (13) | 2<br>1 | 4–5<br>3 | 5<br>5 | 5<br>5 | 5<br>4 | 4<br>3 | 5<br>5 | 1<br>0 | 1<br>0 |
| (9) | 2<br>1 | 4–5<br>3 | 5<br>5 | 5<br>5 | 5<br>3–4 | 5<br>4–5 | 5<br>4–5 | 1<br>0 | 2<br>1 |
| (8) | 2<br>1 | 4–5<br>4 | 5<br>4 | 5<br>5 | 5<br>4 | 4<br>3 | 5<br>5 | 0<br>0 | 1<br>0 |
| (17) | 2<br>1 | 5<br>4 | 5<br>5 | 5<br>5 | 5<br>4 | 3<br>2 | 5<br>5 | 0<br>0 | 3<br>2 |

Table B-continued

| Active compound | Active compound applied kg/hectare | Post-emergence test Echinoch- loa | Chenopo- dium | Sinap- is | Urtica | Matri- caria | Dau- cus | Cotton | Wheat |
|---|---|---|---|---|---|---|---|---|---|
| 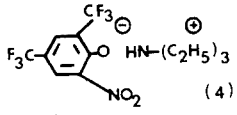 (4) | 2<br>1 | 5<br>3–4 | 5<br>4 | 5<br>5 | 5<br>4 | 4<br>3 | 5<br>5 | 1<br>0 | 2<br>1 |

It will be understood that the specification and examples are illustrative but not limitative of the present invention and that other embodiments within the spirit and scope of the invention will suggest themselves to those skilled in the art.

What is claimed is:

1. 2,4-bis-(trifluoromethyl)-6-nitrophenol compound of the formula

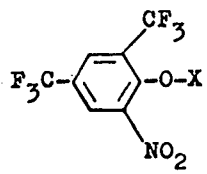

wherein
X is hydrogen or an equivalent of an alkali or alkaline earth metal.

2. Compound as claimed in claim 1 wherein X is hydrogen.

3. Compound as claimed in claim 1 wherein X is an equivalent of an alkali or alkaline earth metal.

* * * * *